United States Patent [19]
Tang et al.

[11] Patent Number: 5,864,042
[45] Date of Patent: Jan. 26, 1999

[54] PROCESS FOR PREPARATION OF A 4-AMINO-5-MERCAPTO-3-SUBSTITUTED-[1,2,4]TRIAZOLE COMPOUND

[75] Inventors: Ping W. Tang; Francesco DeBellis, both of Rochester, N.Y.

[73] Assignee: Eastman Kodak Company, Rochester, N.Y.

[21] Appl. No.: 10,009

[22] Filed: Jan. 21, 1998

[51] Int. Cl.[6] .................................................. C07D 249/12
[52] U.S. Cl. ......................................................... 548/263.8
[58] Field of Search ........................................... 548/263.8

[56] References Cited

U.S. PATENT DOCUMENTS 4,675,280 6/1987 Kaneko et al. .
5,302,496 4/1994 Romanet et al. .

OTHER PUBLICATIONS

Annalon der Chemie und Phamzie, 1960, 637, 135–145.
Zeitschrift fur Chemie, 1969, 9, 111.

*Primary Examiner*—Patricia L. Morris
*Attorney, Agent, or Firm*—Arthur E. Kluegel

[57] ABSTRACT

The invention provides a process for preparing a 4-amino-5-mercapto-3-substituted-[1,2,4]triazole comprising reacting a thiocarbohydrazide with a carboxylic acid in the presence of an organic solvent and a boron compound having the formula

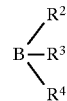

where $R^2$, $R^3$, and $R^4$ are independently selected from the group consisting of hydrogen, hydroxy, amino, alkyl, aryl, alkoxy, and aryloxy groups. The process provides a safer low temperature process for preparing the desired compound.

14 Claims, No Drawings

PROCESS FOR PREPARATION OF A 4-AMINO-5-MERCAPTO-3-SUBSTITUTED-[1,2,4]TRIAZOLE COMPOUND

FIELD OF THE INVENTION

The present invention pertains to an improved method for the preparation of a 4-amino-5-mercapto-3-substituted-[1,2,4]triazole using a thiocarbohydrazide and a carboxylic acid as starting materials.

BACKGROUND OF THE INVENTION 3,6-disubstituted-1H-pyrazolo[3,2-c][1,2,4]triazole couplers are important couplers for photographic products. They are, however, difficult to synthesize. Only a few practical synthetic methods to these couplers are known in the art. One of the preferred synthetic routes involves the preparation of the intermediate: 3,6-disubstituted-7H-[1,2,4]triazolo[3,4-b][1,3,4]thiadiazine(2).

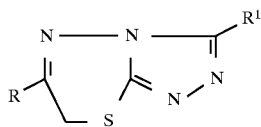

The intermediate 2 can be prepared from the intermediate 1 (4-amino-5-mercapto-3-substituted [1,2,4]trizole), which is the subject of this invention, and an alpha-haloketone as illustrated by the following equation:

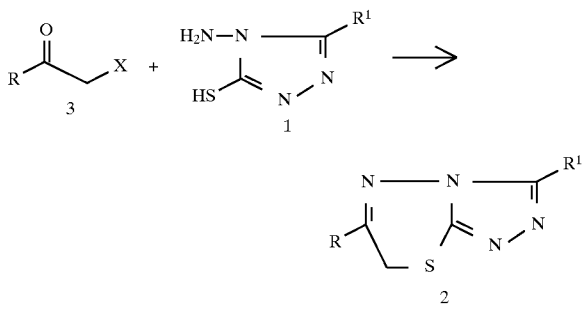

The intermediate compound 1 can be prepared according to Hans Beyer (Annalon der Chemie und Phamzie, 1960, 637, 135–145) and Westphal et al (Zeitschrift fur Chemie, 1969, 9, 111) by using thiocarbohydrazide and a carboxylic acid as follows:

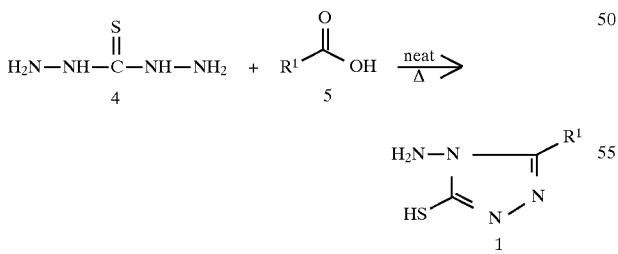

This method uses no solvent. The two starting materials 4 and 5 were heated at a high (melting) temperature in their neat state. The described method suffers many disadvantages:

(1) This method is effective only when the carboxylic acid is liquid. The reaction can be very difficult if the carboxylic acid is a solid;

(2) Thiocarbohydrazide 4 is an explosive and a highly hazardous material. A reaction operated at high temperature involving 4 without a solvent is very difficult because all the solid starting materials are not mixed evenly. As a result, local overheat could occur and explosion could result;

(3) The reaction produces low yield of the intermediate 1 or no product at all. Extensive work-up is needed to obtain a reasonably pure final product.

A problem to be solved is to provide a safer low temperature process for preparing a 4-amino-5-mercapto-3-substituted-[1,2,4]triazole.

SUMMARY OF THE INVENTION

The invention provides a process for preparing a 4-amino-5-mercapto-3-substituted-[1,2,4]triazole comprising reacting a thiocarbonhydrazide with a carboxylic acid in the presence of an organic solvent and a boron compound having the formula

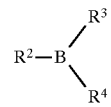

where $R^2$, $R^3$, and $R^4$ are independently selected from the group consisting of hydrogen, hydroxy, amino, alkyl, aryl, alkoxy, and aryloxy groups.

The process of the invention provides a safer low temperature process for preparing the desired compound.

DETAILED DESCRIPTION OF THE INVENTION

The process of the invention is generally as described in the Summary of the Invention. The process may be depicted as follows:

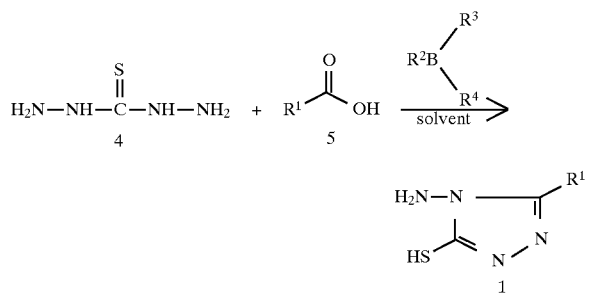

The substituent $R^1$ corresponds to the fragment desired on the ultimate pyrazolotriazole compound or the intermediate 1. It may be hydrogen or a substituent. Suitable examples of substituents are the general substituents as described hereafter. Desirably, the substituent is an alkyl or aryl group, especially those alkyl groups having branching at the alpha and/or beta carbon atoms such as phenoxyacetamide-1,1,2,2-tetramethyl-ethylene groups. Examples of suitable $R^1$ groups are:

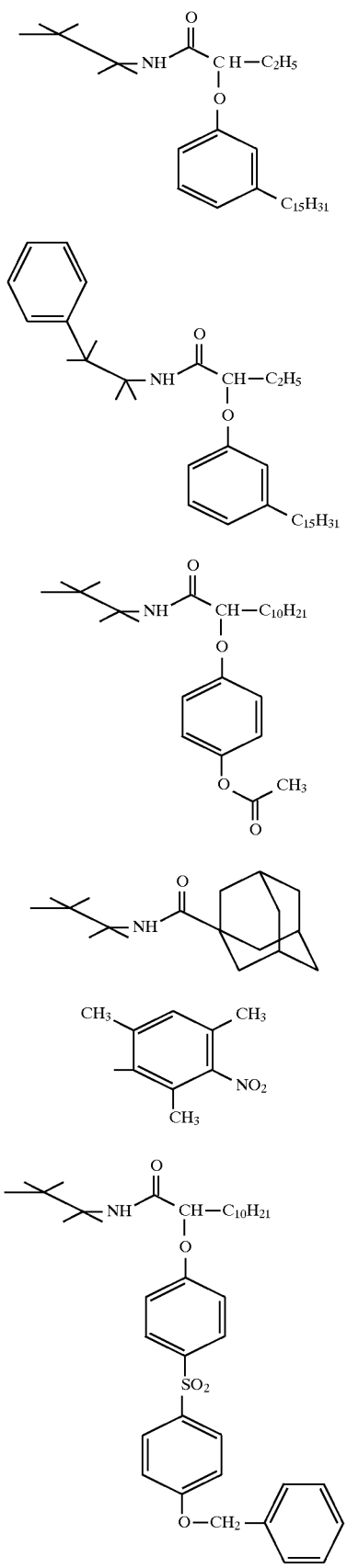
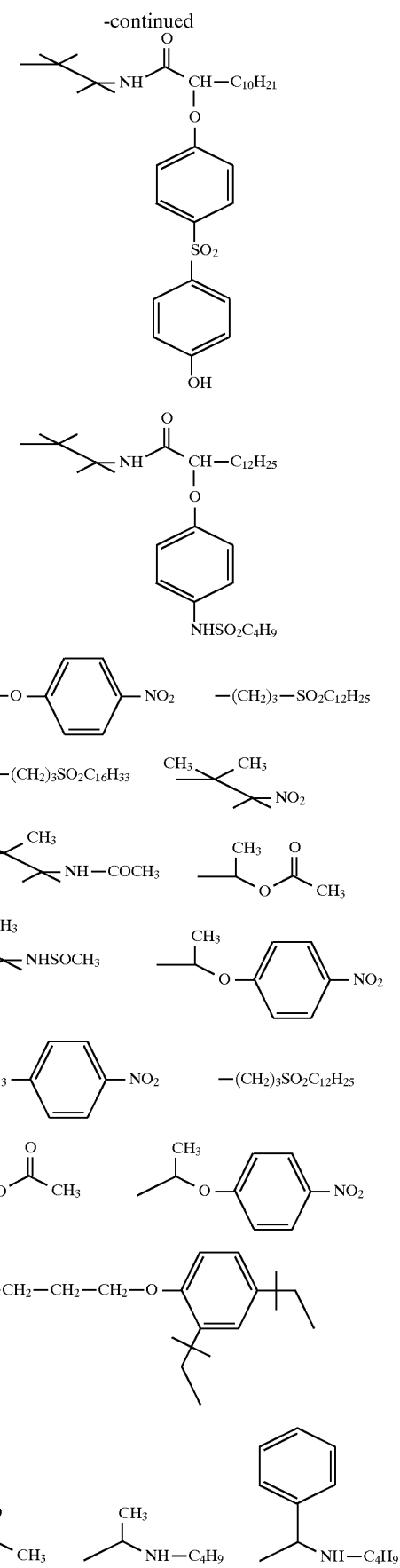

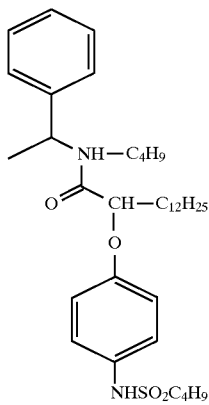

$R^2$, $R^3$, and $R^4$ are independently selected from hydrogen, hydroxy, amino, alkyl, aryl, alkoxy, and aryloxy groups. Desirably, they are independently selected from hydrogen, alkyl groups containing halogen, alkoxy or aryloxy substituents, aryl groups and hydroxy. Particular examples of substituents are:

$C_nX_{2n+1}$ where n=1–20 and X=halogen, o-alkyl, o-aryl such as

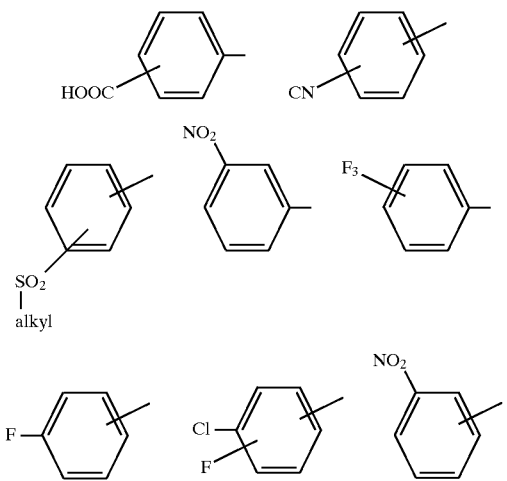

A desirable boron compound is 3-nitrobenzeneboronic acid:

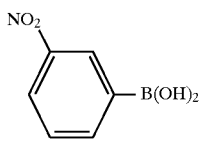

Other examples are:

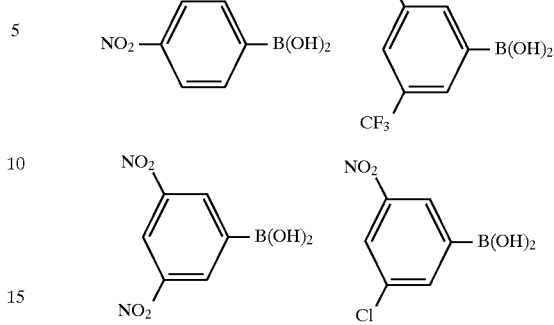

The boron compound acts in a catalytic manner to facilitate the formation of the desired intermediate. The boron compound is suitably present in an amount of from 1 to 50 wt % based on thiocarbohydrazide, typically 10–25 wt %. Since the boron compound is not part of the end product, it need not be provided in any particular stochiometric quantity.

The solvent employed may be any organic solvent employable in organic syntheses. Examples are one or more aromatic hydrocarbons such as benzene, toluene, and xylene; heteroaromatic compounds; nitriles; amides; esters; ethers; dimethylsulfoxide and hexamethylphosphoroustriamide (HMPA). Toluene, benzene, xylene, mesitylene, butyronitrile, acetonitrile, dioxane, or tetrahydrofuran are readily employed.

The temperature for the reaction is desirably from room temperature to 200° C., suitably 30°–150° C., and typically 60°–140° C. The reaction time is normally from 0.5 to 48 hrs, typically 4 to 24 hrs and conveniently 6 to 24 hrs.

Unless otherwise specifically stated or when the term "group" is used, it is intended throughout this specification, when a substituent group contains a substitutable hydrogen, to encompass not only the substituent's unsubstituted form, but also its form further substituted with any group or groups as herein mentioned, so long as the group does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic allyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy,p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

SYNTHETIC EXAMPLES

Example 1

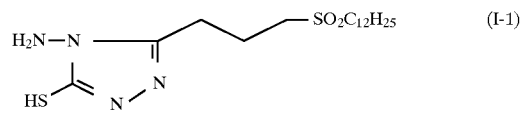

4-amino-3-[3-(dodecylsulfonyl)propyl]-5-mercapto-[1,2,4]triazole.

To a mixture of 4.9 g (47 mmol) of thiocarbohydrazide and 15 g (47 mmol) of 4-(dodecylsulfonyl)butanoic acid in 30 ml of toluene was added 0.8 g (4.7 mmol) of 3-nitrobenzeneboronic acid. The mixture was heated at reflux for 24 hr. Upon cooling, the thick precipitate was collected, rinsed with a small amount of acetonitrile (10 ml), dried in vacuo to yield 16 g (87.4%) of the desired product as a white solid. All of the analytical data confirmed the assigned structure.

Example 2

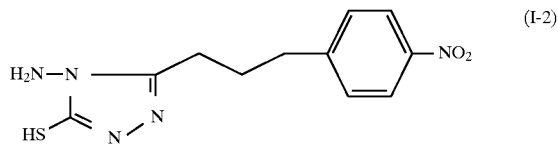

4-amino-5-mercapto-3-[3-(4-nitrophenyl)propyl][1,2,4]triazole.

To a mixture of 4.9 g (47 mmol) of thiocarbohydrazide and 9.8 g (47 mmol) of 4-nitrophenylbutanoic acid in 30 mL of toluene was added 0.8 g (4.7 mmol) of 3-nitrobenzeneboronic acid. The mixture was heated at reflux for 24 hr. The reaction was cooled and the reaction mixture was allowed to settle. The supernatant liquid was decanted. To the residual solid was added 50 mL of acetonitrile. The mixture was stirred for 30 minutes. The solid was collected, rinsed with 10 mL of acetonitrile and dried in vacuo to yield 8.5 g (65.4%) of the desired product as a white sandy material. All the analytical data confirmed the assigned structure.

Example 3

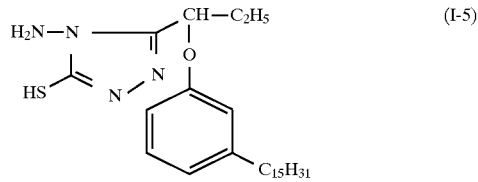

4-Amino-5-mercapto-3-[1-(3-pentadecylphenoxy)propyl][1,2,4]triazole

To a mixture of 2.65 g (25 mmol) of thiocarbohydrazide and 9.77 g (25 mmol) of 2-(3-pentadecylphenoxy)butanoic acid in 30 mL of toluene was added 0.42 g (2.5 mmol) of 3-nitrobenzene boronic acid was heated at reflux for 24 hr. The reaction was cooled and the reaction was allowed to settle. The supernatant liquid was decanted. To the residual solid was added 20 mL of acetonitrile. The mixture was stirred for 15 minutes. The solid was collected, rinsed with 5 mL of cold acetonitrile and dried in vacuo to afford 7.20 g (60.4%) of the desired product as a white solid. Analytical data are consistent with the assigned structure.

Example 4

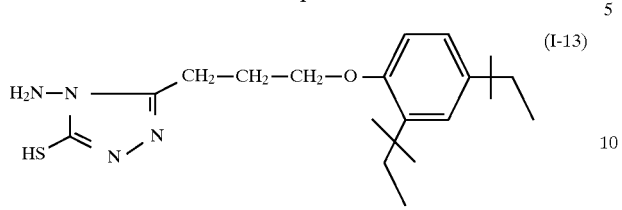

4-Amino-5-mercapto-3-[3-(2,4-di(tert-pentyl)phenoxy)propyl][1,2,4]triazole.

The preparation was conducted according to the same procedure as described in the Example 1. All the analytical data of the product obtained in this reaction are consistent with the assigned structure.

Structure Examples

The following are examples of intermediates that can be made in accordance with the invention:

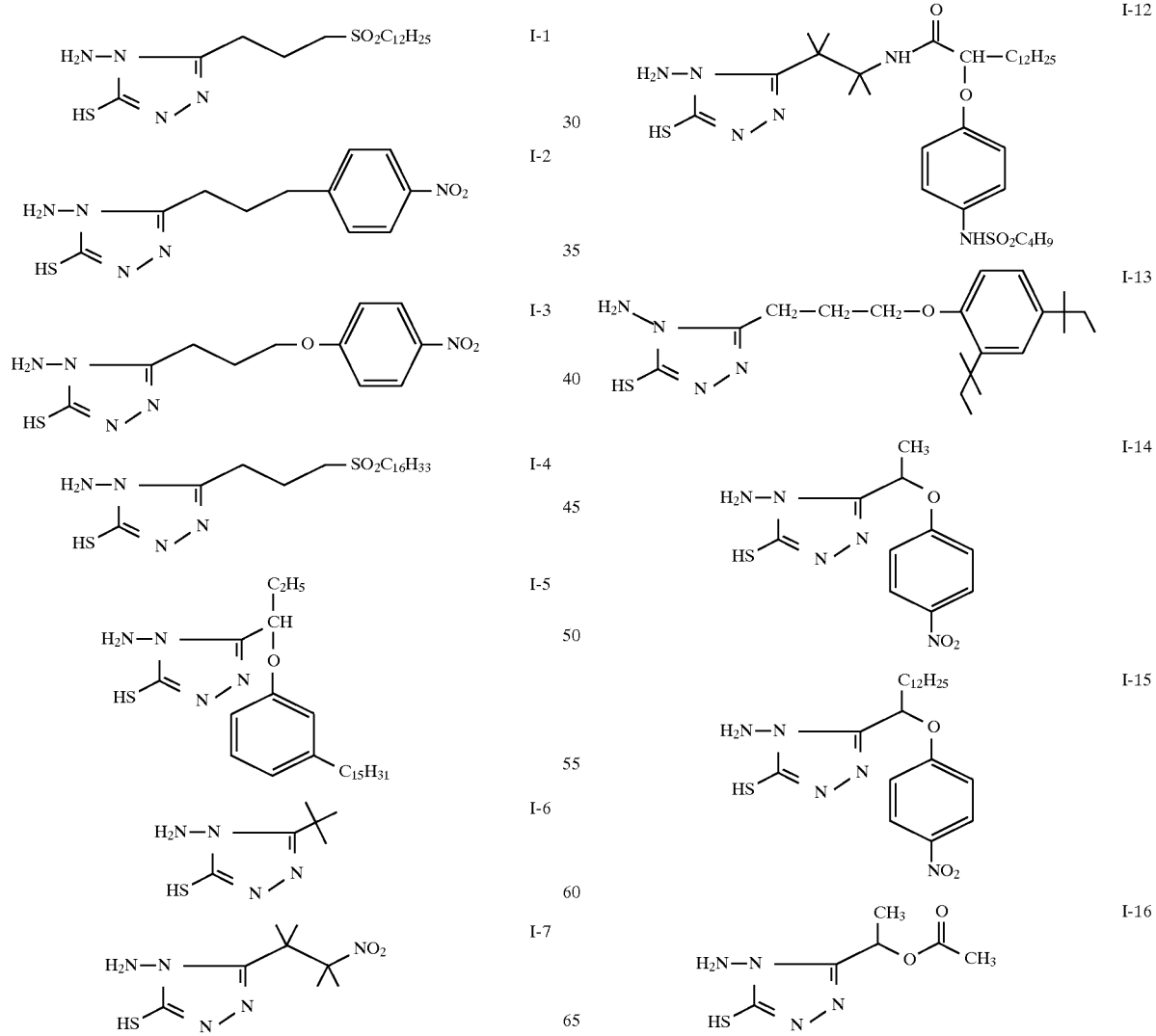

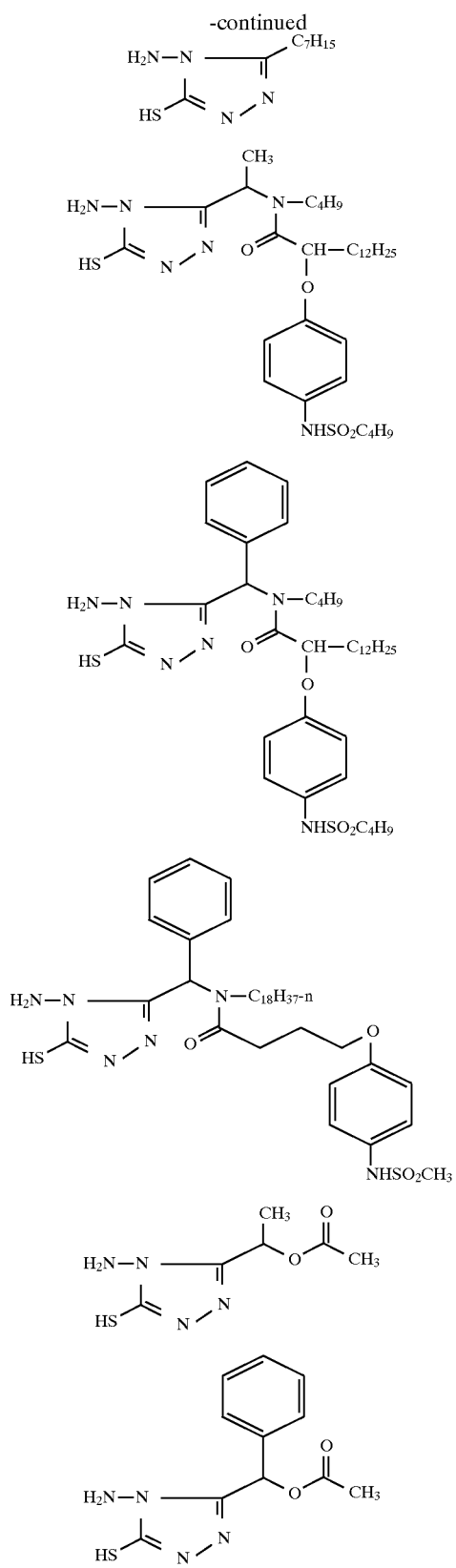

The invention has been described in detail with particular reference to certain preferred embodiments thereof, but it will be understood that variations and modifications can be effected within the spirit and scope of the invention.

What is claimed is:

1. A process for preparing a 4-amino-5-mercapto-3-substituted-[1,2,4]triazole comprising reacting a thiocarbohydrazide with a carboxylic acid in the presence of an organic solvent and a boron compound having the formula

where $R^2$, $R^3$, and $R^4$ are independently selected from the group consisting of hydrogen, hydroxy, amino, alkyl, aryl, alkoxy, and aryloxy groups.

2. The process of claim 1 wherein the solvent is selected from the group consisting of aromatic compounds, nitriles, ethers, amides, and esters.

3. The process of claim 2 wherein the solvent is selected from the group consisting of benzene, toluene, xylene, hexamethylphosphorustriamide, dimethylsulfoxide, dimethylformamide, tetrahydrofuran, and heteroaromatic compounds.

4. The process of claim 3 wherein the solvent is toluene.

5. The process of claim 1 wherein $R^2$, $R^3$, and $R^4$ are independently selected from the group consisting of hydroxy and aryl groups.

6. The process of claim 5 wherein $R^2$, and $R^3$ are hydroxy and $R^4$ is a phenyl group.

7. The process of claim 6 wherein $R^4$ is a nitrophenyl group.

8. The process of claim 1 wherein the temperature of the reaction is from room temperature to 200° C.

9. The process of claim 8 wherein the temperature of the reaction is from 30°–150° C.

10. The process of claim 9 wherein the temperature of the reaction is from 60°–140° C.

11. The process of claim 1 wherein the amount of

present is from 1 to 20 wt % of compound 4.

12. The process of claim 4 wherein $R^2$, $R^3$, and $R^4$ are independently selected from the group consisting of hydroxy and aryl groups.

13. The process of claim 12 wherein $R^2$, and $R^3$ are hydroxy and $R^4$ is a nitrophenyl group.

14. The process of claim 13 wherein the reaction is performed at a temperature between 30° C. to 150° C.

* * * * *